United States Patent [19]

Christini et al.

[11] Patent Number: 5,836,974
[45] Date of Patent: Nov. 17, 1998

[54] REAL-TIME AND ADAPTIVE METHOD AND SYSTEM FOR SUPPRESSING A PATHOLOGICAL NON-CHAOTIC RHYTHM

[75] Inventors: David J. Christini, Allston; James J. Collins, Bringhton, both of Mass.

[73] Assignee: Trustees of Boston University, Boston, Mass.

[21] Appl. No.: 768,458

[22] Filed: Dec. 18, 1996

Related U.S. Application Data

[60] Provisional application No. 60/008,782 Dec. 18, 1995.
[51] Int. Cl.⁶ ..................................................... A61N 1/39
[52] U.S. Cl. .................................................................. 607/5
[58] Field of Search ................................. 607/4, 5, 6, 7, 607/8, 9, 14

[56] References Cited

U.S. PATENT DOCUMENTS 5,201,321  4/1993  Fulton .
5,447,520  9/1995  Spano et al. ................................. 607/5

FOREIGN PATENT DOCUMENTS

WO 94/04219  3/1994  WIPO .

Primary Examiner—Scott M. Getzow
Attorney, Agent, or Firm—Samuels, Gauthier, Stevens & Reppert

[57] ABSTRACT

Low-dimensional real-world chaotic or non-chaotic dynamical systems are controlled by a model-independent control technique that does not require knowledge of the system's governing equations or a pre-control learning stage. Control is applied to a real-world system by estimating the desired unstable periodic fixed point, determining the value of a perturbation that will be made to a readily-accessible system parameter, entering the perturbation to the system, and adaptively adjusting the control sensitivity in order to force the system toward its unstable periodic fixed point. Control is repeated periodically and maintained indefinitely or for a predetermined length of time.

30 Claims, 3 Drawing Sheets

REAL-TIME AND ADAPTIVE METHOD AND SYSTEM FOR SUPPRESSING A PATHOLOGICAL NON-CHAOTIC RHYTHM

PRIORITY

This application claims priority from provisional application Ser. No. 60/008,782 filed Dec. 18, 1995.

FIELD OF THE INVENTION

This invention relates to a method and system that can be used to eliminate unwanted dynamics in real-world, low-dimensional chaotic and non-chaotic dynamical systems. More specifically, this invention relates to a real-time, adaptive, model-independent control technique for suppressing pathological non-chaotic physiological rhythms, such as atrioventricular nodal alternans.

BACKGROUND OF THE INVENTION

Traditional model-based control techniques and model-independent techniques have been proposed to control low-dimensional chaotic and non-chaotic dynamical systems. Nevertheless, there are drawbacks to both traditional control techniques and model-independent techniques which make them impracticable for certain real-world systems. Traditional control techniques are limited because they require knowledge of a system's governing equations in order to achieve control. In the case of real-world systems, however, these equations are often unknown. Current model-independent techniques are better suited than model-based techniques for "black box" systems (i.e., systems where the governing equations are unknown) because they extract all necessary control information by monitoring the system as it fluctuates before attempting to control it. This monitoring is generally thought of as a learning stage. This learning stage is undesirable in real-world systems where unwanted dynamics must be eliminated quickly, and the time required for a learning stage is not available.

SUMMARY OF THE INVENTION

Therefore, a need has arisen for a control technique which requires neither knowledge of a system's governing equations nor a pre-control learning stage.

It is one object of the present invention to use model-independent control techniques that do not require a pre-control learning stage to suppress pathological non-chaotic rhythms by stabilizing an unstable system about its unstable periodic orbit (fixed point). These control techniques apply parameter perturbations that are directly proportional (according to a proportionality constant g) to the difference between the system's state point and the system's unstable period-1 fixed point.

It is another object of the present invention to use model-independent control techniques that do not require a pre-control learning stage to suppress a pathological cardiac, rhythm known as atrioventricular (AV) nodal alternans. For AV nodal alternans suppression, the parameter perturbed is the HA interval; importantly, this parameter is experimentally accessible.

In one embodiment, the present invention comprises a method for eliminating unwanted dynamics in real-world dynamical systems which have an unstable periodic orbit whose dynamics are directly dependent on a perturbable system parameter. The method implements a control technique which adaptively estimates an unstable periodic fixed point for the dynamical system and sets a control sensitivity parameter. A perturbation signal (to be applied to the perturbable system parameter) is then determined using the control sensitivity parameter. These control perturbation signals are estimated and applied to the perturbable system parameter for as long as control is desired.

In one specific embodiment, the present invention comprises a method for eliminating AV nodal alternans, which is a pathological alternation in the conduction time of cardiac impulses through the AV node. Initially the method estimates the unstable period-1 fixed point for the conduction time through the AV node. Based on the estimated unstable period-1 fixed point, the control technique calculates the required timing of a controlled heart stimulus. The control stimulus is then input to the heart. The conduction time of the control stimulus through the AV node is monitored, and the unstable period-1 fixed point is adjusted based on the response of the heart to the control stimulus. The method is then repeated using the adjusted value of said unstable period-1 fixed point.

In another specific embodiment, the present invention comprises a system for stabilizing a conduction time for cardiac impulses through the atrioventricular node. The system includes a controller for estimating the unstable period-1 fixed point for the conduction time of a cardiac impulse through the atrioventricular node and a means for calculating a time at which a control stimulation will be input to the heart based on the estimated unstable period-1 fixed point. An implantable stimulator is used to input the control stimulation to the heart via an implantable device. Finally, the system includes means for monitoring the conduction time of the control stimulation through the AV node. The controller adjusts the unstable period-1 fixed point based on the response of the heart to said control stimulation.

Figure 1:
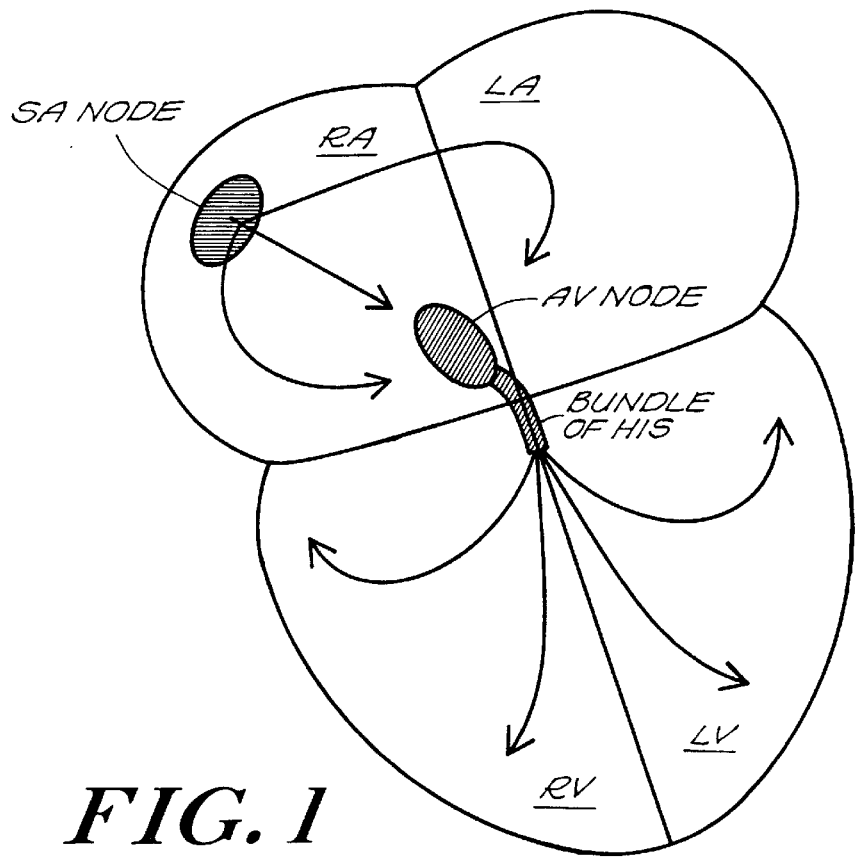
FIG. 1 is a diagram of the heart schematically showing the cardiac impulse conduction path.

The features and objects of the present invention, and the manner of attaining them is explained in detail in the following DETAILED DESCRIPTION OF THE PREFERRED EMBODIMENTS.

DETAILED DESCRIPTION OF THE PREFERRED EMBODIMENTS

The teachings of the embodiments of the invention eliminate unwanted dynamics in real-world, low-dimensional chaotic and non-chaotic dynamical systems through use of a model-independent, real-time, adaptive control technique. These teachings are applicable to any system in which the variable to be controlled has an unstable periodic orbit (UPO) whose dynamics are directly dependent on a perturbable system parameter. Control methods and systems according to embodiments of the invention stabilize a system's state point about a targeted UPO by applying parameter perturbations which repeatedly direct the system's state point towards the targeted UPO.

Generally, the control technique according to embodiments of the present invention stabilizes the unstable periodic fixed point $\xi^* = [\chi^*, \chi^*]^T$ (where superscript T denotes transpose and $[\chi^*, \chi^*]^T$ is a 2×1 column vector) of a system that can be described by the difference equation $$\chi_{n+1} = f(\chi_n, p_n)$$

where $\chi_n$ is the current value (scalar) of one measurable system variable, $\chi_{n+1}$ is the next value of the same variable, and $p_n$ is the value (scalar) of an accessible system parameter p at index n. The control technique perturbs p such that $$p_n = \bar{p} + \delta p_n, \quad (1)$$

where $\bar{p}$ is the mean parameter value, and $\delta p_n$ is a perturbation given by $$\delta p_n = \frac{\chi_n - \chi_n^*}{g_n} \quad (3)$$

where $\chi_n^*$ is the current estimate of $\chi^*$ and $g_n$ is the control sensitivity at index n. This alters the $n^{th}$ state point via a perturbation made to an accessible system parameter p at each index n.

Initially, g is set to an arbitrary value. Optimal control performance occurs when the initial value for g is close to the ideal value for g. However, the control technique according to the present invention can converge to the appropriate value for g from an arbitrary initial value for g. Further, when control is initiated (i.e., at index $n_1$), $\chi^*$ is estimated as $$\chi_{n1}^* = \sum_{i=0}^{N-1} \frac{\chi_{n1-i}}{N}, \quad (4)$$

where N is the number of consecutive $\chi$ iterates averaged into the $\chi^*$ estimate. After each iteration, following the next measurement of $\chi$ (i.e., $\chi_{n+1}$), the technique adaptively re-estimates the values for $\chi^*$ and g. The new estimate for $\chi^*$ is given by $$\chi_{n+1}^* = \sum_{i=0}^{N-1} \frac{\chi_{n-i+1}}{N}, \quad (5)$$

This adaptability allows for the control of non-stationary systems and eliminates the need for a pre-control learning stage.

Following each control intervention, the magnitude of g is also adapted. Initially a determination is made as to whether the desired control precision has been achieved. The desired control precision has been achieved if for each i ($0 \leq i \leq N-1$), $$|\chi_{n-i+1} - \chi_{n-i}^*| < \epsilon. \quad (6)$$

where $\chi_{n-i}^*$ is the estimate of $\chi^*$ which the control technique targeted for $\chi_{n-i+1}$.

If the desired control precision has not been achieved, then the magnitude of g is decreased by a factor p (i.e., $g_{n+1} = g_n/\rho$, where $\rho$ is the adjustment factor) if for each i ($0 \leq i \leq N-1$)

$$|\chi_{n-i+1} - \chi_{n-i}^*| > W \quad (7)$$

where $$W = D \exp\left(\frac{-(n+1-n_1)}{\tau}\right), \quad (8)$$

where $n_1$ is the initial control index, and D and $\tau$ are defined below. W defines the maximum allowable distance between a given $\chi$ and its corresponding estimate $\chi^*$. This distance decays exponentially from an initial value D to force convergence to the fixed point, where $\tau$ governs the worst-case convergence rate. The values for D and $\tau$ will vary depending upon the system being controlled. If equation (6) is satisfied, it indicates that the control perturbations were not large enough to force any of the previous N values for $\chi$ within the required proximity W. Thus, to achieve control, the perturbation size is increased by decreasing the magnitude of g. Otherwise, if neither equation (5) nor (6) is satisfied and if $$\sum_{i=0}^{N-1} |\chi_{n-i+1} - \chi_{n-i}^*| > \sum_{i=N}^{2N-1} |\chi_{n-i+1} - \chi_{n-i}^*|, \quad (9)$$

then the magnitude of g is increased by $\rho$ (i.e., $g_{n+1} = g_n \rho$). If equation (8) is satisfied it indicates that the N most recent $\chi$ values are cumulatively further from their respective estimated values, $\chi^*$, than the N previous $\chi$ values. Thus, $\chi$ is not properly approaching $\chi^*$. The magnitude of g is not adapted if both equation (6) and equation (8) are not satisfied (such a condition indicates that the state point is properly approaching the fixed point).

This technique is practical for real-world systems, because it is: (1) model-independent, (2) real-time, and (3) adaptive. Model-independence is vital because accurate quantitative models of real-world systems are rarely available. Real-time operation is vital because time for pre-control analysis is often unavailable. Finally, adaptability is vital because non-stationarities are common in real-world systems. Importantly, this technique is: (1) applicable to a wide range of parameter regimes, (2) relatively insensitive to initial values of the proportionality constant g, (3) robust to additive noise, (4) capable of stabilizing higher-order unstable periodic orbits, and (5) applicable to many different systems. These features establish the practicality of this control technique for real-world systems. For example, the control technique could be used to stabilize a cardiac system experiencing atrioventricular nodal alternans, to suppress tremors in body limbs and appendages, and to control networks of neurons.

Implementation of the control technique will now be explained in the context of one preferred embodiment where the technique is used to suppress atrioventricular (AV) nodal alternans. The intrinsic rhythm of the mammalian heart is controlled by electrical impulses which originate from a specialized group of cells within the right atrium known as the sinoatrial (SA) node. Referring to FIG. 1, RA, LA, RV, and LV stand for right atrium, left atrium, right ventricle, and left ventricle, respectively. After initiation at the SA node, a cardiac impulse propagates through the atrial tissue to the AV node, which is the electrical connection between the atria and the ventricles. The impulse then passes through the AV node and enters the bundle of His, from where it is distributed throughout the ventricular tissue. The AV node is an essential component of cardiac function because it generates a propagation delay which allows ventricular filling and thus facilitates the efficient pumping of blood.

There are several conditions during which the heart diverges from its normal rhythm. One such condition is atrioventricular nodal alternans, a pathological cardiac condition characterized by a beat-to-beat alteration (period-2 rhythm) in the time required for a cardiac impulse to pass through the AV node (i.e. AV nodal conduction time). A short AV nodal propagation time is followed by a long AV nodal propagation time, which is followed by another short AV nodal propagation time, etc. This conduction time is approximated by the atrial-His (AH) interval, which is the time between cardiac impulse excitation of the atria (specifically, the lower interatrial septum) and cardiac impulse excitation of the bundle of His.

Several experimental studies have shown that the AH interval is a function of the time interval between the bundle of His activation and the next atrial activation (which is equivalent to the time interval between when one cardiac impulse leaves the AV node and the next impulse reaches the entry of the AV node). This time interval, known as the AV nodal recovery time, is referred to as the HA interval. The cells of the AV node require a minimum amount of time to recover between cardiac impulses. AV nodal alternans is usually caused by cardiac impulses which reach the AV node at a rate faster than the minimum recovery time required by the AV node cells (i.e., HA is less than the required nodal recovery time). Therefore, an impulse arriving at the AV node entrance before the cells have recovered will propagate through the AV node at a slower rate than it normally would. However, once the next impulse arrives, the cells of the AV node will generally have had time to recover (due to the slow propagation of the previous impulse) and the impulse propagates quicker than the previous impulse. This leads to two alternating values for AH, the defining characteristic of AV nodal alternans. A graphical depiction of AV nodal alternans is given by FIG. 2, which shows the AV nodal conduction time as a function of beat number n. It can be seen from FIG. 2 that at about n=250, or at 250 beats, the AH interval bifurcates from a constant (period-1) rhythm into an alternans rhythm.

One of the problems with the alternans rhythm is that it affects the time for ventricular filling. That is, during a long AH, a large volume of blood will fill the heart (ventricles), while during a short AH, only a small volume of blood will fill the heart. Because the amount of blood pumped through the body is proportional to the volume of blood in the heart, normal circulation is thus disrupted during AV nodal alternans.

One cause of AV nodal alternans is reentrant tachycardia, which occurs when an electrical impulse that has passed through the AV node normally, rebounds back into the atria, stimulating another beat, thereby significantly shortening the HA time. Reentrant tachycardia can be eliminated by the surgical destruction of the electrical pathway between the ventricles and the atria that conducts a re-entrant cardiac impulse. The destruction of conducting cardiac tissue is undesirable. Additionally, the procedure must be repeated if the pathway is not completely eliminated or if a new pathway develops. The teachings of the preferred embodiments of the present invention enable a condition such as atrioventricular nodal alternans to be controlled without the destruction of cardiac tissue.

A method for suppressing AV nodal alternans according to one embodiment of the present invention is explained with reference to FIGS. 3 and 4. In general, the method of the present invention involves maintaining the AV nodal conduction time, AH, at a constant or near constant value. Note that AH in the following description is the measurable system variable denoted by $\chi$ in the above generically described control method (N=2). By maintaining AH at a constant value, the unstable period-1 fixed point, is stabilized. AH is estimated at each beat according to:

$$AH^*_n = \frac{AH_n + AH_{n-1}}{2} \quad (9)$$

where $AH_n$ is the AV nodal conduction time of beat n, and $AH_{n-1}$ is the AV nodal conduction time of beat (n-1). This fixed point $AH^*_n$ is the average value of the two prior AV nodal conduction times. Note that Eq. 9 is a simplification of Eq. 3 suitable for period-2 rhythms. AH is the difference in time from when the cardiac impulse is detected at the AV node entrance to when the cardiac impulse is detected at the AV node exit. Therefore, in step 305, AH is monitored for each cardiac impulse. As will be explained in more detail in conjunction with FIG. 5, this monitoring can be accomplished by, for example, detecting each cardiac impulse as it passes the entrance and the exit of the AV node.

In step 310, in order to screen anomalous data, an initiation difference measure, $\Delta AH^i_n$, ($\Delta AH^i_n = |AH_n - AH_{n-1}|$) is calculated over N consecutive heart beats. In step 315, a determination is made, based on the calculated initiation difference measure, whether or not control should be initiated. In the embodiment of FIG. 3, this involves initiating control after N successive beats in which $\Delta AH^i$ is greater than or equal to the predetermined value $Q^i$. In still another embodiment, the difference measure is averaged over N consecutive heart beats and the averaged difference measure is compared with the predetermined value $Q^i$. Steps 310 and 315 help ensure control will not be initiated unless necessary. In a simplified embodiment, control could be initiated based on whether the difference in AV nodal conduction time between the two most recent beats was larger than the difference measure.

Figure 3:
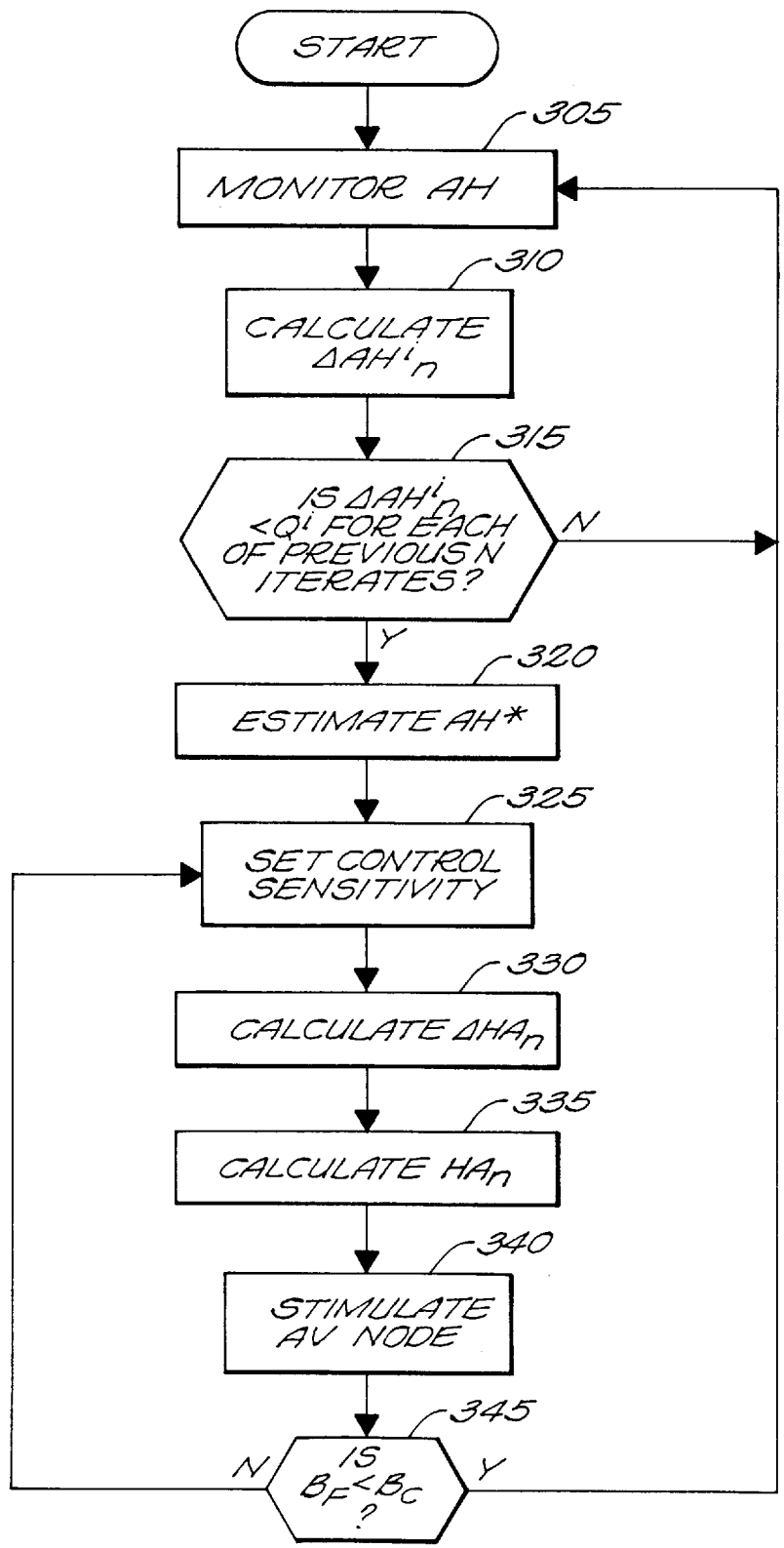
FIG. 3 is a flowchart showing a method of suppressing AV nodal alternans according to one embodiment of the present invention.
Figure 4:
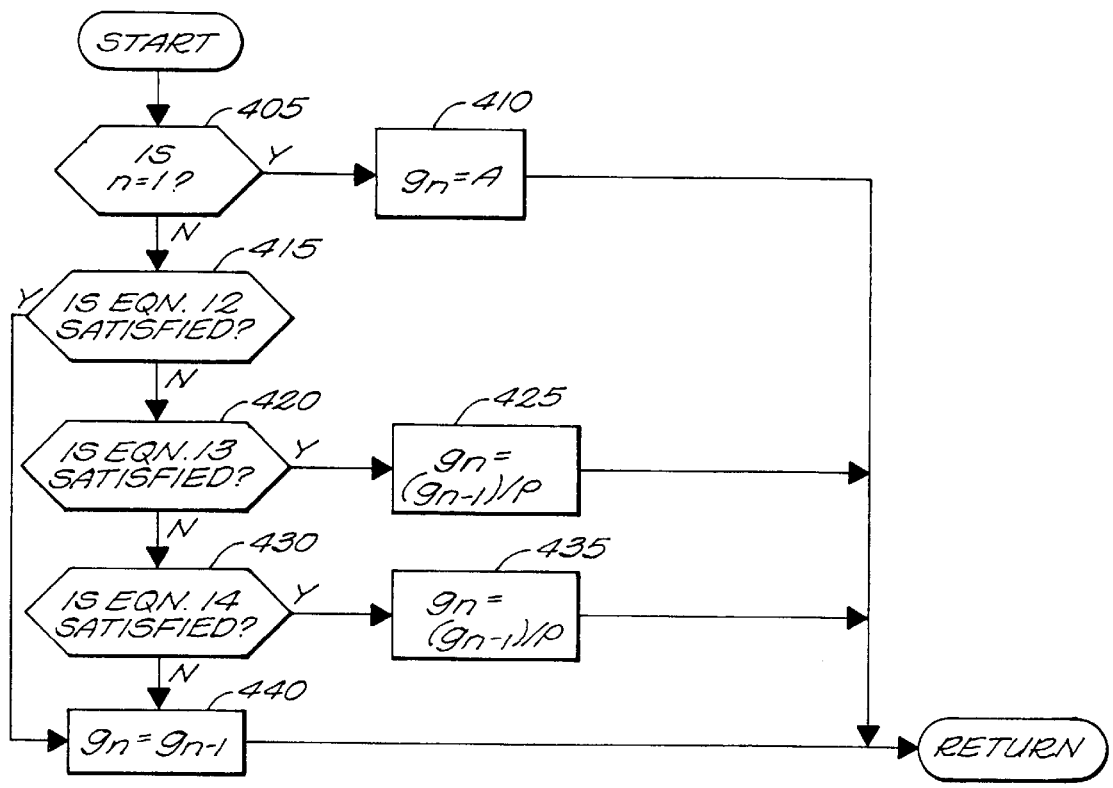
FIG. 4 is a flowchart showing a method for adjusting the control sensitivity, g, according to one embodiment of the present invention.

The method of FIG. 3 forces the heart toward the unstable period-one fixed point. In order to do this, the heart is stimulated electrically with a voltage pulse of amplitude V volts and duration M seconds, which will vary depending on, inter alia, the age of the patient, the sex of the patient, and the physical condition of the heart. The determination of values for V and M will be made by a cardiologist. It is important to note that the values of V and M are not critical elements of this invention. It is more important to determine the appropriate time at which the stimulus is input to the heart.

Figure 2:
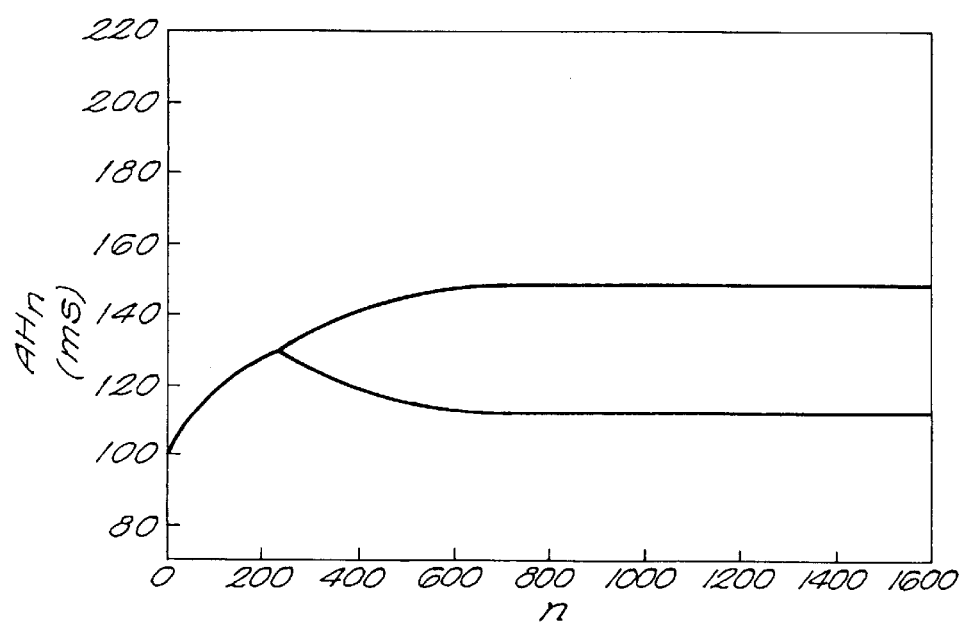
FIG. 2 is a graphical representation of AV nodal alternans showing a bifurcated AH interval.

Returning to FIG. 3, if the result of step 315 indicates control is necessary, model-independent control is initiated in step 320 by calculating an estimate, AH* for the accessible system variable AH. Referring to FIG. 2, for the $n^{th}$ beat, $AH^*_n$, is initially estimated as the midpoint of the two AH branches as indicated in equation 9 above. In step 325, the control sensitivity g is set. The control sensitivity is set according to the method which will be explained in conjunction with FIG. 4. For the initial control perturbation, g is set to an arbitrary value.

Referring to FIG. 3, once the control sensitivity is set, step 330 calculates a value for the perturbation $\Delta HA$ by entering the set value of g into equation 3. For the case of AV nodal alternans occurring in the cardiac environment, equation 3 reduces to:

$$\Delta HA_{n+1} = \frac{AH_n - AH^*_n}{g} \quad (10)$$

The perturbable parameter in the cardiac environment is HA, the time period between when a cardiac impulse exits the AV node and the next cardiac impulse enters the AV node. Importantly, this parameter is both experimentally accessible and perturbable. Thus, in step 335, a value for HA is determined. The perturbation $\Delta HA$ is entered into equation 1, which becomes $$HA_n = \overline{HA} + \Delta HA_n \tag{11}$$

where $\overline{HA}$ is the heart's pre control natural value of HA (Note that if $AH_n > AH^*_n$, then $\Delta HA_n > 0$). In this case, Eq. 11 corresponds to interval lengthening. Interval lengthening cannot occur, because the hearts natural-beat will pre-empt the stimulus. If a stimulus is pre-empted, it should not be delivered. Thus, stimuli will only be delivered on average, every other beat. This value $HA_n$ is essentially the time that the method will wait from the time that a cardiac impulse is sensed at the exit of the AV node to the time that a control stimulus is entered to the heart. That is, in order to gain control of the heart, the method of the present invention actually speeds up the heart by reducing the HA interval. This ensures that the natural impulses produced in the body do not interfere with the pulses introduced via the stimulation of this method.

In step 340, the method stimulates the heart at the time $HA_n$. This stimulation involves entering a stimulus (amplitude V volts, duration M seconds) to the heart in order to initiate propagation across the AV node. As discussed above, the value for V is typically determined by a cardiologist based on a number of different factors. As will be explained in more detail in conjunction with FIG. 5, this stimulation may be accomplished by, for example, an implantable stimulating electrode positioned near the SA node of the heart.

The method, in step 345, next determines whether or not to continue to control the system. The number of beats that have occurred since control was initiated, $B_C$, is compared with a predetermined number of beats $B_F$. In another embodiment, $B_C$ is the amount of time that has elapsed since control was initiated. Whether it is a number of beats or a time period, the value for $B_F$ will generally be determined by a cardiologist. When $B_C$ is at least equal to $B_F$ (i.e., $B_C \geq B_F$), control is removed and the method returns to step 301.

If, in step 345, it is determined that the predetermined number of beats of the predetermined elapsed time has not occurred, the method returns to step 305.

Step 325 for setting and adapting the control sensitivity (i.e., the proportionality constant) g will now be discussed. As discussed earlier, several equations are used in order to determine how g is adjusted. Referring to FIG. 4, step 405 first queries whether this will be the first control iteration. If it is, step 410 sets g to the value A, a predetermined value, determined by a cardiologist, which depends on inter alia the age of the patient, the sex of the patient, and the physical condition of the heart.

If it is not the first control iteration, the method queries in step 415 whether the system is operating within a predetermined control precision, $\epsilon$. To do this, the method first defines a second difference measure, $\Delta\Delta H$, between $AH_n$ and $AH^*_n$ as $\Delta\Delta H = AH_n - AH^*_n$ (note that this is the numerator of equation 10). This difference measure is then compared to the control precision. In this system, equation 5 reduces to $$|AH_{n-i+1} - AH^*_{n-i}| < \epsilon \tag{12}$$

This equation is satisfied, the atrioventricular conduction time is properly converging and, thus, no adjustments to g are necessary.

If the system is not operating within the predetermined control precision, the method determines how to adjust g to reach that precision. Equation 4, with variable substitution for the cardiac system, becomes $$|AH_{n-i+1} - AH^*_{n-i}| > D \exp \frac{-(n-n_1)}{\tau} \tag{13}$$

where:

$$D = \frac{\max(AH) - \min(AH)}{4}$$

where $\max(AH)$ and $\min(AH)$ are the maximum and minimum pre-control AH values. $\tau$ governs the convergence of the system and may have a value of 100.

In step 420, the comparison of equation 13 is made. If the comparison indicates equation 13 is satisfied, $g_n$ is decreased by a predetermined percentage in step 425

$$g_n = \frac{g_{n-1}}{\rho}$$

where $\rho$ is set at, for example, 1.05. Other values could be used depending upon particular patient conditions.

If equation 13 is not satisfied, the method in step 430, determines if the following equation, which is Eq. 5 with variable substitution, is satisfied:

$$\sum_{i=0}^{N-1} |AH_{n-i+1} - AH^*_{n-i}| > \sum_{i=N}^{2N-1} |AH_{n-i+1} - AH^*_{n-i}| \tag{14}$$

If the result of step 430 indicates that equation 10 is satisfied, then the magnitude of $g_n$ is increased by a predetermined percentage value in step 435.

$$g_n = (g_{n-1})(\rho)$$

where $\rho = 1.05$.

If steps 420 and 430 indicate that neither equation 9 nor equation 10 is satisfied, then g is not adapted (step 440).

Figure 5:
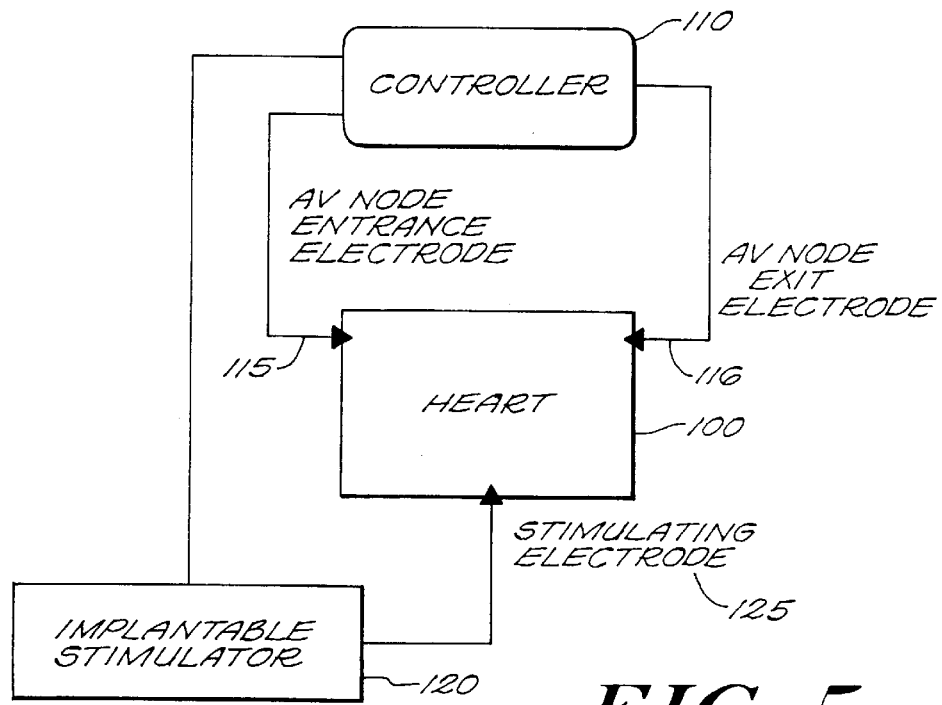
FIG. 5 is a block diagram showing a system for suppressing AV nodal alternans according to one embodiment of the present invention.

A system for suppressing AV nodal alternans according to one embodiment of thus invention is shown in FIG. 5. Controller 110 monitors heart 100 by two electrodes 115, 116 that are implanted to measure the cardiac impulse at the entrance and exit of the AV node, respectively. Controller 110 may be implantable and is microprocessor based, and performs the measurement of the AV nodal conduction time by calculating the difference in time between the first impulse at the entry electrode and the second impulse at the exit electrode. Further, controller 110 compares two consecutive propagation times to determine whether it is necessary to initiate control. As explained in conjunction with steps 310 and 315 above, if the times differ by a value greater than Q, the controller initiates control over the system. Controller 110 also implements Eqs. 7–12 to determine the initial value of HA that will be entered into this system. Controller 110, upon sensing a cardiac impulse at the exit of the AV node by electrode 116, starts timing for the interval $HA_n$. Upon reaching the value of $HA_n$, the controller instructs a device 120 to electrically stimulate the heart with a voltage pulse, (amplitude V volts, duration M seconds). In one embodiment, device 120 is a stimulator. The electrical stimulation may be delivered to the heart by an implantable stimulating electrode 125. The exact locations for implanting stimulator 120, electrodes 115, 116 and 125 would be decided by cardiologists in conjunction with the manufacturers of the various devices.

Further, controller 110 also implements step 345 of the method to determine whether to remove control. That is, controller 110 keeps the count $B_C$ and compares it with $B_F$ following each control perturbation.

Although this invention has been explained with reference to specific embodiments, it is not intended that the invention be limited thereto. Rather, the invention is only limited by the claims which follow.

We claim:

1. A method of stabilizing a non-chaotic alternating conduction time for cardiac impulses through the atrioventricular node comprising the steps of:
    initiating a control sequence in response to the development of a non-chaotic alternation in conduction time, said control sequence comprising:
    estimating the unstable period-1 fixed point for said non-chaotic alternating conduction time through the atrioventricular node;
    calculating a time at which a control stimulation will be input to the heart based on said estimated unstable period-1 fixed point and a control sensitivity parameter;
    inputting a control stimulation to the heart;
    monitoring the conduction time to the control stimulation through the atrioventricular node;
    adjusting said unstable period-1 fixed point based on said response of the heart to said control stimulation; and
    adapting said control sensitivity parameter automatically:
    wherein the steps of said control sequence are repeated in real-time to achieve stabilization of said conduction time.

2. The method of claim 1 further comprising determining whether it is necessary to initiate said control sequence.

3. The method of claim 2 wherein said determining comprises:
    sensing a cardiac impulse at the entrance of said atrioventricular node;
    sensing said cardiac impulse at the exit of said atrioventricular node;
    measuring the time between sensings as the atrioventricular nodal conduction time of said cardiac impulse.

4. The method of claim 3 wherein said determining further comprises:
    calculating an initiation difference measure between the atrioventricular nodal conduction time of a cardiac impulse and an atrioventricular nodal conduction time of a previous cardiac impulse;
    comparing said initiation difference measure with a predetermined value; and
    initiating control if said initiation difference measure is greater than or equal to the predetermined value.

5. The method of claim 3 wherein said determining further comprises:
    calculating an initiation difference measure between the atrioventricular nodal conduction time of a cardiac impulse and an atrioventricular nodal conduction time of a previous cardiac impulse;
    comparing said initiation difference measure with a predetermined value; and
    initiating control if said initiation difference measure is greater than or equal to the predetermined value for a predetermined number of consecutive beats.

6. The method of claim 3 wherein said determining further comprises:
    calculating an average initiation difference measure between the atrioventricular nodal conduction time of a cardiac impulse and an atrioventricular nodal conduction time of a previous cardiac impulse for a predetermined number of beats;
    comparing said average initiation difference measure with a predetermined value;
    initiating control if said average initiation difference measure is greater than or equal to said predetermined value.

7. The method of claim 1 wherein estimating the unstable period-1 fixed point for said conduction time through the atrioventricular node comprises:
    measuring atrioventricular nodal conduction times of two consecutive cardiac impulses; and,
    calculating the midpoint of said consecutive atrioventricular nodal conduction times.

8. The method of claim 1 wherein calculating a time at which said control stimulation will be input comprises:
    calculating a perturbation for a time period defined between when a cardiac impulse exits the atrioventricular node and when a next cardiac impulse enters the atrioventricular node;
    adding said perturbation to a pre-control mean time interval.

9. The method of claim 1 wherein inputting a control stimulation to the heart comprises:
    detecting a cardiac impulse at the exit of the atrioventricular node;
    measuring a predetermined period of time after detection of the cardiac impulse at the exit of the atrioventricular node to determine a time at which the control stimulation will be input to the heart; and
    inputting the control stimulation of a predetermined amplitude and duration to the heart.

10. The method of claim 1 wherein monitoring the conduction time of the control stimulation through the atrioventricular node comprises:
    sensing said control stimulation at the entrance of said atrioventricular node;
    sensing said control stimulation at the exit of said atrioventricular node; and,
    measuring the time between sensings.

11. The method of claim 1 further comprising determining if control should be removed, said determining comprising:
    counting a number of control stimulations which have been input;
    comparing said number of control stimulations to a predetermined number;
    wherein if said number of control stimulations is greater than or equal to said predetermined number, control is removed.

12. The method of claim 1 further comprising determining if control should be removed, said determining comprising:
    measuring an elapsed time since input of a first control stimulation;
    comparing said elapsed time to a predetermined elapsed time;
    wherein if said elapsed time is greater than or equal to said predetermined elapsed time, control is removed.

13. The method of claim 1 wherein said step of adjusting said period-1 unstable fixed point comprises:
    measuring atrioventricular nodal conduction times of a control stimulation and a previous stimulation impulse; and,
    calculating an average of said atrioventricular nodal conduction times.

14. A method of eliminating unwanted dynamics in real-world chaotic and non-chaotic dynamical systems which have an unstable periodic orbit and are directly dependent on a perturbable system parameter comprising:

initiating a control sequence in response to instability in the system, said control sequence comprising:
  estimating an unstable periodic fixed point for said dynamical system;
  determining a perturbation signal using said control sensitivity parameter;
  inputting said perturbation signal to said perturbable system parameter; and
  adapting a control sensitivity parameter automatically; and
repeating said control sequence in real-time to achieve elimination of said unwanted dynamics.

15. The method of claim 14 wherein said real-world dynamical system comprises a higher-order pathological rhythm in a cardiac system.

16. The method of claim 14 wherein said real-world dynamical system comprises a tremor in body limbs and appendages.

17. The method of claim 14 wherein said real-world dynamical system involves networks of neurons.

18. A real-time system for stabilizing a conduction time for cardiac impulses through the atrioventricular node comprising:
  a controller for estimating the unstable period-1 fixed point for said conduction time through the atrioventricular node;
  means for calculating a time at which a control stimulation will be input to the heart based on said estimated unstable period-1 fixed point and a control sensitivity parameter;
  an implantable stimulator for inputting a control stimulation to the heart;
  means for monitoring the conduction time of the control stimulation through the atrioventricular node; and
  means for automatically adapting said control sensitivity parameter;
  said controller adjusting said unstable period-1 fixed point based on the response of the heart to said control stimulation.

19. The system of claim 18 further comprising means for determining whether it is necessary to initiate control.

20. The system of claim 19 wherein said means for determining comprises:
  a first electrode positioned at the entrance of said atrioventricular node for sensing a cardiac impulse;
  a second electrode positioned at the exit of said atrioventricular node for sensing said cardiac impulse; and,
  said controller measuring the time between sensings as the atrioventricular nodal conduction time of said cardiac impulse.

21. The system of claim 20 wherein said means for determining further comprises:
  said controller calculating an initiation difference measure between the atrioventricular nodal conduction time of a cardiac impulse and an atrioventricular nodal conduction time of a previous cardiac impulse;
  said controller comparing said initiation difference measure with a predetermined value; and
  said controller initiating control if said initiation difference measure is greater than or equal to the predetermined value.

22. The system of claim 20 wherein said means for determining further comprises:
  said controller calculating an initiation difference measure between the atrioventricular nodal conduction time of a cardiac impulse and an atrioventricular nodal conduction time of a previous cardiac impulse;
  said controller comparing said initiation difference measure with a predetermined value; and,
  said controller initiating control if said initiation difference measure is greater than or equal to the predetermined value for a predetermined number of consecutive beats.

23. The system of claim 20 wherein said means for determining further comprises:
  said controller calculating an average initiation difference measure between the atrioventricular nodal conduction time of a cardiac impulse and an atrioventricular nodal conduction time of a previous cardiac impulse for a predetermined number of beats;
  said controller comparing said average initiation difference measure with a predetermined value;
  said controller initiating control if said average initiation difference measure is greater than or equal to said predetermined value.

24. The system of claim 18 wherein estimating the unstable period-1 fixed point for said conduction time through the atrioventricular node comprises:
  a first electrode positioned at the entrance of said atrioventricular node for sensing a cardiac impulse;
  a second electrode positioned at the exit of said atrioventricular node for sensing said cardiac impulse;
  said controller measuring the time between sensings as the atrioventricular nodal conduction time of said cardiac impulse; and,
  said controller measuring atrioventricular nodal conduction times of two consecutive cardiac impulses and calculating the midpoint of said consecutive atrioventricular nodal conduction times.

25. The system of claim 18 wherein said means for calculating a time at which said control stimulation will be input comprises:
  said controller calculating a perturbation for a time period defined between when a cardiac impulse exits the atrioventricular node and when a next cardiac impulse enters the atrioventricular node; and,
  said controller adding said perturbation to a pre-control mean time interval.

26. The system of claim 18 further comprising an electrode positioned at the exit of the atrioventricular node;
  said controller receiving a signal from said electrode indicating a cardiac impulse has passed the exit of the atrioventricular node and measuring a predetermined period of time after said cardiac impulse has passed the exit of the atrioventricular node thereby determining a time at which the control stimulation will be input to the heart; and
  said implantable stimulator inputting the control stimulation of a predetermined amplitude and duration to the heart.

27. The system of claim 18 wherein monitoring the conduction time of the control stimulation through the atrioventricular node comprises:
  a first electrode for sensing said control stimulation at the entrance of said atrioventricular node;
  a second electrode for sensing said control stimulation at the exit of said atrioventricular node; and,
  said controller measuring the time between sensings.

28. The system of claim 18 further comprising means for determining if control should be removed, said means for determining comprising:

said controller counting a number of control stimulations which have been input;

said controller comparing said number of control stimulations to a predetermined number;

wherein if said number of control stimulations is greater than or equal to said predetermined number, control is removed.

29. The system of claim 18 further comprising means for determining if control should be removed, said means for determining comprising:

said controller measuring an elapsed time since input of a first control stimulation;

said controller comparing said elapsed time to a predetermined elapsed time;

wherein if said elapsed time is greater than or equal to said predetermined elapsed time, control is removed.

30. The system of claim 18 wherein said controller measures atrioventricular nodal conduction times of a control stimulation and a previous stimulation impulse to the heart; and, said controller calculates an average of said atrioventricular nodal conduction times as an adjusted unstable period-1 fixed point.

* * * * *